United States Patent
Kjaer et al.

(10) Patent No.: US 12,320,745 B2
(45) Date of Patent: Jun. 3, 2025

(54) POROUS MEMBRANE SENSOR ASSEMBLY

(71) Applicant: RADIOMETER MEDICAL APS, Brønshøj (DK)

(72) Inventors: Thomas Kjaer, Brønshøj (DK); Willy Lindegaard Andersen, Brønshøj (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 125 days.

(21) Appl. No.: 17/756,375

(22) PCT Filed: Dec. 21, 2020

(86) PCT No.: PCT/EP2020/087498
§ 371 (c)(1),
(2) Date: May 24, 2022

(87) PCT Pub. No.: WO2021/123442
PCT Pub. Date: Jun. 24, 2021

(65) Prior Publication Data
US 2023/0020985 A1    Jan. 19, 2023

(30) Foreign Application Priority Data
Dec. 19, 2019 (DK) .......................... PA2019001514

(51) Int. Cl.
*G01N 21/31* (2006.01)
*G01N 21/77* (2006.01)
*G01N 33/49* (2006.01)

(52) U.S. Cl.
CPC ............. *G01N 21/31* (2013.01); *G01N 33/49* (2013.01); *G01N 2021/773* (2013.01); *G01N 2021/7763* (2013.01)

(58) Field of Classification Search
CPC .. G01N 21/31; G01N 33/49; G01N 2021/773; G01N 2021/7763
See application file for complete search history.

(56) References Cited

U.S. PATENT DOCUMENTS

2010/0051481 A1* 3/2010 Mayer ................ G01N 15/0826
                                                         205/793
2010/0267066 A1    7/2010 Hosokawa et al.
(Continued)

FOREIGN PATENT DOCUMENTS

CN       1997885 A    11/2007
CN     102802797 A    11/2012
(Continued)

OTHER PUBLICATIONS

Nguyen, Nam-Trung et al., "Micromixers—a review," Journal of Micromechanics and Microengineering, vol. 15, pp. R1-R16 (2005).
(Continued)

*Primary Examiner* — Mary Ellen Bowman
*Assistant Examiner* — Joshua M Carlson
(74) *Attorney, Agent, or Firm* — Frost Brown Todd LLC

(57) ABSTRACT

The present invention relates a sensor assembly for analyzing a complex fluid sample. The sensor assembly comprises a sample chamber for holding the complex fluid sample, the sample chamber being defined by chamber walls and having an inlet and an outlet defining a direction of flow from the inlet towards the outlet for fluid handling in the sample chamber. The sample chamber comprises a first sample space and a second sample space. The second sample space comprises a porous membrane sensor element for detecting an analyte in a continuous fraction of the complex fluid sample. The porous membrane sensor element comprises a porous membrane with a front side defining a sensor surface for contacting the fluid sample, the sensor surface facing towards the second sample space, the porous membrane comprising pores extending from respective openings at the sensor surface into the porous membrane. The pores are configured with regard to the analyte for diffusive fluid communication with the second sample space. The sample (Continued)

chamber further comprises a flow-perturbing element arranged upstream of the second sample space, between the first sample space and the second sample space.

19 Claims, 2 Drawing Sheets

(56) References Cited

U.S. PATENT DOCUMENTS

| | | | | |
|---|---|---|---|---|
| 2018/0328842 | A1* | 11/2018 | Kjaer | G01N 33/721 |
| 2019/0157061 | A1* | 5/2019 | Datwani | H01J 49/0445 |
| 2019/0246959 | A1* | 8/2019 | Ionescu | A61B 10/0064 |

FOREIGN PATENT DOCUMENTS

| | | |
|---|---|---|
| EP | 0 638 805 A2 | 2/1995 |
| WO | WO 01/89675 A2 | 11/2001 |
| WO | WO 2006/014410 A1 | 2/2006 |
| WO | WO 2010/124001 A1 | 10/2010 |
| WO | WO 2019/197308 A1 | 10/2019 |

OTHER PUBLICATIONS

International Search Report of International Application No. PCT/EP2020/087498, dated Mar. 19, 2021 (three pages).
Written Opinion of the International Search Authority for International Application No. PCT/EP2020/087498 (seven pages).
English translation of Chinese Office Action for International Application No. CN202080088458.0, Issued on Oct. 24, 2024, 10 pages.
English translation of Japanese Office Action for International Application No. JP 2022-538174, mailed on Jul. 7, 2023, 4 pages.
European Examination Report for International Application No. EP 20838534.4, mailed on Jul. 31, 2024, 2 pages.

* cited by examiner

POROUS MEMBRANE SENSOR ASSEMBLY

This application is a national stage filing under 35 U.S.C. § 371 of International Application No. PCT/EP2020/087498, filed on Dec. 21, 2020, which claims priority of Danish Patent Application No. PA201901514, filed on Dec. 19, 2019. The contents of these applications are each incorporated herein by reference.

The present invention relates in one aspect to a sensor assembly for analyzing a complex fluid sample with regard to one or more analytes, the sensor assembly comprising a sample chamber for holding the complex fluid sample. According to a further aspect, the invention relates to a sensor assembly for detecting high molecular weight components in a continuous fraction of a complex fluid sample presented in a sample chamber. According to a further aspect, the invention relates to a sensor assembly comprising a porous membrane sensor arranged in the sample chamber. According to a further aspect, the invention relates to a sensor assembly for detecting high molecular weight components in a continuous fraction of a complex fluid sample presented in a sample chamber comprising a porous membrane sensor. According to a further aspect, the invention relates to a sensor assembly for detecting high molecular weight components in a continuous fraction of a complex fluid sample presented in a sample chamber comprising a porous membrane sensor and for detecting further analytes of the same complex fluid sample by means of further sensors arranged in the sample chamber. According to a yet further aspect, at least the high molecular weight components are detected by optical probing.

BACKGROUND OF THE INVENTION

Detecting an analyte in a complex fluid containing continuous and discontinuous fractions is a challenging, but frequently encountered measurement problem. Typically the measurements involve steps of sample preparation including separation, e.g. by filtration, sedimentation and/or centrifugation, and subsequent detection measurement steps using chemical indication reactions and/or physical interactions sensitive to the analyte in question. An intricate challenge in this context is often the preparation and presentation of a proper sample for the detection without compromising the measurement, in particular if a volume of the available sample is small, and if the fluid to be analyzed is very complex. On top of that, very often in such a situation, multiple parameters are to be determined on the same sample, which imposes additional constraints of integrating a given measurement for the detection of an analyte with measurements of other parameters.

Therefore, there is a need for a highly sensitive, yet simple and fast technique allowing for the selective detection of an analyte in a complex fluid, which is furthermore adapted for easy integration with other measurement techniques for determining multiple parameters of the same sample. The desired technique is furthermore required to provide for gentle separation, extraction, and/or isolation of the analyte for the detection measurements, i.e. without compromising the remaining fractions of the fluid to be analyzed.

Such a detection technique is relevant for various industries, ranging from food industry, over wastewater treatment, to pharmaceutical applications and medical devices, where known techniques often require large sample volumes and time-consuming analysis procedures.

One example for the application of such a measurement technique is in relation to the detection of an analyte in body fluids, such as a patient's blood sample. The analyte can be any of a laboratory's test parameters for body fluid analysis, which is detectable by light, e.g. spectrophotometry. As one source of interference in the analysis of blood, hemolysis may affect the measurement of a number of blood parameters as determined in blood parameter analyzers. Disregarding a level of free hemoglobin in the blood sample may thus mislead an unaware person and as a result provide a wrong diagnosis based on the affected blood parameter value. However, reliably determining a level of free hemoglobin present in the plasma fraction of a whole blood sample hitherto involved a complex process requiring separation of the plasma fraction from the cellular components and a subsequent analysis of the separated plasma fraction. Such a procedure is time consuming and may be prohibitive in cases where only very small samples are available at a time, such as in neonatal care with a continued monitoring of blood parameters in the infant. Other approaches for measuring components present in the plasma fraction in whole blood involve the separation of a plasma fraction from cellular components by microfiltration techniques in e.g. a microfluidic device, prior to analysis of the plasma fraction in a dedicated measurement in the microfluidic device. For example, a recent scientific article by Archibong et al. and published in Sensing and Bio-Sensing Research 3 (2015), p. 1-6, discloses a miniature measuring chamber for optically analyzing a plasma fraction that has been separated from a whole blood sample. In this type of device, a miniature microfluidic chamber is attached to the interface of an optical fiber. The bottom of the microfluidic chamber consists of a porous membrane that allows fluids and chemical compounds to flow inside the device, while at the same time filtering out undesired particles. The inside of the microfluidic chamber receiving the filtrate can be optically probed through a single optical fiber in normal-incidence reflection geometry. However, due to clogging issues, the disclosed device is most useful as a disposable rather than for continued and repetitive use, since a complete washout of a sample after measurement may be difficult or at least very time-consuming and unreliable, at the further risk of cross-contamination between subsequent samples. Furthermore, in this particular type of device, additional challenges for obtaining quantitative results from the optical probing may arise, due to pressure-induced deformation of the filtration membrane resulting in a change of the optical path for probing the filtrate.

In a further example, namely applications in food industries, such as dairy industry, most traditional methods of filtering and detecting comprise filter paper, sieves and the like for visual inspection, spectrometry or bacterial counting of the residues with the above-mentioned disadvantages of requiring relatively large sample volumes and involving time-consuming measuring procedures that are detrimental to the sample, and that are incompatible with integrated multiple-parameter measurements to be performed on the same sample. Similar challenges are also encountered in the field of environmental technologies, such as wastewater analysis and treatment, where most traditional methods of filtering and detecting comprise filter papers, sieves and the like for spectrometry and bacterial counting of the residues.

Filtration-based approaches have several disadvantages when used for analyzing e.g. whole blood samples. Filtration devices inherently rely on a fluid flow of at least the filtrate through the pores of the filter from a sample feed to a filtrate analysis/measurement chamber. In through-flow geometries, the retentate (here the red blood cells) gradually clogs the filtration pores. In crossflow geometries, the retentate is lead along the surface of the filtering membrane, thereby reducing but not removing the problem with clogging, especially if the system is intended for repetitive use (more than 10-100 samples). Crossflow geometry also induces friction and shear interaction between the retentate and the surface of the filtering device.

An improved separation and measurement technique addressing these issues is disclosed in the co-pending international patent applications by the applicant, WO 2017/085162 A1, WO 2017/085180 A1, and WO 2019/197308 A1, which are hereby incorporated by reference.

Again, a particularly challenging field of application is the analysis of body fluids in a point-of-care set-up. Modern point-of-care analyzers for analyzing multiple parameters in body fluid samples, such as for the analysis of arterial blood, are subject to severe requirements and constraints of patient safety, user friendliness, short measurement times in the range of a minute or below, reliability/reproducibility, precision of the quantitative output, as well as compliance with quality management systems and safety directives for medical measurement apparatus to only name a few. The precise and compliant results have to be obtained on very small amounts of sample fluid (typically less than 100 µl, or even less than 50 µl) in agreement with the above-mentioned requirements and constraints. Most advanced point-of-care analyzer systems are therefore designed around an automated fluid handling and measurement infrastructure with a compact sensor assembly at its core. Such sensor assemblies are for repetitive use and typically have a sample space defined by sample chamber walls with miniaturized high precision sensors directly integrated in at least one of the walls. An example of such a sensor assembly for body fluids is e.g. disclosed in the European patent specification EP 2 147 307 B1. The sensor assembly of EP 2 147 307 B1 comprises electrochemical and optical sensor elements, which is particularly suitable for simultaneously measuring a plurality of different parameters in body fluid samples, such as blood parameters. It is therefore desirable that a new measurement technique fulfilling the above-stated needs for highly sensitive, simple and selective detection of an analyte in a complex fluid should be suited for integration with such a sensor assembly having a sample channel width in the millimeter range and a sample channel height in the sub-millimeter range.

A device for detecting an analyte in a fluid sample by optical probing is described in the above-mentioned application WO2019197308A1 by the applicant, wherein a porous sensor element is arranged in a chamber wall of a sample chamber comprising for holding the fluid sample. The sensor surface has open pores and faces towards the sample chamber to contact the fluid sample, and to receive in the pores analytes from at least the continuous fraction of a complex fluid sample by means of diffusion.

One merit of the present invention resides in the insight that the accuracy, reproducibility, and reliability of the measurements obtained when operating a porous membrane device for detecting an analyte in a complex fluid may be strongly affected by the diffusive transport of the analyte in question from the complex fluid sample into the pores of the porous membrane, where the actual measurement by optical probing is performed.

Therefore, there still is a need for an improved device and method for the detection of an analyte in a fluid with a fast and reliable response, which can be implemented in a miniaturized manner that would facilitate integration within an automated point-of-care analyzer system for body fluids. More generally, there still is a need for an improved device and method for the detection of substances in a fraction of a complex fluid, such as a whole blood sample with a fast and reliable response, which is adapted for miniaturization and integration in a fluid analyzer system, in particular an analyzer system for multiple-parameter measurements on the same fluid sample.

According to one aspect an object of the present invention is therefore to provide an improved detection device and/or method overcoming at least some of the disadvantages of known devices, sensors, systems and/or methods for specific detection of analytes in the continuous fraction of a complex fluid, such as for detecting an analyte in a plasma fraction of a whole blood sample. According to a further aspect, an object of the present invention is to provide such a detection device, which can be miniaturized for integration with a sensor assembly.

SUMMARY OF THE INVENTION

According to one aspect, the invention relates to a sensor assembly for analyzing a complex fluid sample, the sensor assembly comprising: a sample chamber for holding the complex fluid sample, the sample chamber being defined by chamber walls and having an inlet and an outlet defining a direction of flow from the inlet towards the outlet for fluid handling in the sample chamber; wherein the sample chamber comprises a first sample space and a second sample space, the second sample space comprising a porous membrane sensor element for detecting an analyte, the porous membrane sensor element comprising a porous membrane with a front side defining a sensor surface for contacting the fluid sample, the sensor surface facing towards the second sample space, the porous membrane comprising pores extending from respective openings at the sensor surface into the porous membrane, wherein the pores are configured with regard to the analyte for diffusive fluid communication with the second sample space; wherein the sample chamber further comprises a flow-perturbing element arranged upstream of the second sample space, between the first sample space and the second sample space.

In the context of point-of-care measurement systems (in the art also referred to as 'bedsite' systems) and laboratory environments alike, blood gas analysis is oftentimes undertaken by users, such as nurses, who may not be users trained in use of blood gas analyzers. In particular, users' correct placement of a handheld blood sample container, such as a syringe or a capillary tube, at an inlet structure of the blood gas analysis has been found to constitute a challenging aspect in aspiration of the blood sample into the blood gas analyzers. Incorrect positioning or alignment of the blood sample container relative to the inlet structure may not only lead to disturbing delays and/or frustrations in users' daily workflows but may even in result in loss of blood samples or contamination of the blood gas analyzer or its surroundings.

According to a specific aspect of the invention, there is presented use of a system/method according to any of the embodiments herein, for point-of-care (POC) measurement on analyte parameters in body fluids, and in particular in a whole blood sample.

POC measurement is also referred to as 'bed site' measurement in the art. In the present context, the term 'point-of-care measurement' should be understood to mean measurements which are carried out in close proximity to a patient, i.e. measurements that are not carried out in a laboratory. Thus, according to this embodiment, the user of the blood gas analyzer performs measurement of a whole blood sample in a handheld blood sample container in the proximity of the patient, from whom the blood sample is taken, e.g. in the hospital room or ward accommodating the patient's bed, or in a nearby room of the same hospital department. In such use, the level of expertise of the user oftentimes varies from novice to experienced, and the capability of the blood gas analyzer to automatically output instructions matching each individual user's skills on the basis of sensor input is thus particularly beneficial in such environments.

The sensor assembly is useful for analyzing complex fluids comprising a continuous fraction and a discontinuous fraction, in particular for selectively detecting an analyte in the continuous fraction of the complex fluid. The sensor assembly is particularly useful for miniaturization and/or integration in a fluid analyzer set-up for measuring multiple analyte parameters, e.g. in a modern arterial blood analyzer.

The term "complex fluid" as used herein refers to a fluid with a continuous fraction and a discontinuous fraction, such as a liquid fraction and a particulate fraction. Typically, the analyte is a component in the continuous fraction of the complex fluid sample. The fluid to be analyzed thus contains at least a continuous fraction comprising the analyte. The fluid to be analyzed may further contain a discontinuous fraction, i.e. a particulate fraction. The particulate fraction may include, for example, solid particles, debris and other contaminants, biological cells (such as red blood cells) or microorganisms, liquid droplets, gas bubbles, and combinations thereof. The fluid to be analyzed may be a whole blood sample, the plasma fraction of whole blood, spinal cord fluid, urine, pleura, ascites, wastewater, a pre-prepared fluid for any kind of injection, fluids with a constituent possible to detect by optical probing, such as spectroscopy, or a gas such as air, carbon dioxide containing gas, carbon monoxide containing gas.

The analyte may be any substance detectable by a suitable probing technique, such as optical probing, such as further detailed below. For example, the analyte may be a subset of molecules that may be present in the continuous phase of the fluid to be analyzed. For example, when analyzing a whole blood sample, the analyte may be a particular drug, and the measurement may be for determining a drug content in the plasma phase, e.g. to determine drug uptake and adjust dosing of the drug accordingly. In another example of analyzing a whole blood sample, the analyte may be bilirubin for determining a degree of hemolysis. In yet another example of analyzing a whole blood sample, the analyte may be carbon dioxide.

The term "fluid" refers to liquids and/or gases including complex fluids comprising a continuous phase and a discontinuous phase, such as a particulate phase. Examples of relevant fluids to be analyzed using embodiments of the present invention include, but are not limited to body fluids, in particular whole blood sample, the plasma fraction of whole blood, spinal cord fluid, urine, pleura, ascites. Further examples of relevant fluids include wastewater, a pre-prepared fluid for any kind of injection, fluids with a constituent possible to detect by spectroscopy, or a gas such as air, a carbon dioxide containing gas, a carbon monoxide containing gas. The term "sample" refers to the part of the fluid that is used or needed in the analysis with the porous membrane of the invention.

The term "whole blood" refers to blood composed of blood plasma, and cellular components. The plasma represents about 50%-60% of the volume, and cellular components represent about 40%-50% of the volume. The cellular components are erythrocytes (red blood cells), leucocytes (white blood cells), and thrombocytes (platelets). Preferably, the term "whole blood" refers to whole blood of a human subject, but may also refer to whole blood of an animal. Erythrocytes constitute about 90%-99% of the total number of all blood cells. They are shaped as biconcave discs of about 7 µm in diameter with a thickness of about 2 µm in an un-deformed state. The erythrocytes are highly flexible, which allows them to pass through very narrow capillaries, reducing their diameter down to about 1.5 µm. One core component of erythrocytes is hemoglobin, which binds oxygen for transport to the tissues, then releases oxygen and binds carbon dioxide to be delivered to the lungs as waste product. Hemoglobin is responsible for the red color of the erythrocytes and therefore of the blood in total. Leucocytes make up less than about 1% of the total number of all blood cells. They have a diameter of about 6 to about 20 µm. Leucocytes participate in the body's immune system e.g. against bacterial or viral invasion. Thrombocytes are the smallest blood cells with a length of about 2 to about 4 µm and a thickness of about 0.9 to about 1.3 µm. They are cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50%-60% by volume). Plasma is devoid of cells. It contains all coagulation factors, in particular fibrinogen and comprises about 90%-95% water, by volume. Plasma components include electrolytes, lipid metabolism substances, markers, e.g. for infections or tumors, enzymes, substrates, proteins and further molecular components.

The term "wastewater" refers to water that has been used, as for washing, flushing, or in a manufacturing process, and so contains waste products and/or particles and is thus not suitable for drinking and food preparation.

The sample chamber is formed as a channel extending from the inlet to the outlet and includes a first sample space and a second sample space, which are separated from each other by a flow-perturbing element. The first sample space is arranged upstream of the flow-perturbing element as seen in a direction from the inlet to the outlet, between the flow-perturbing element and the inlet, and the second samples space is arranged downstream of the flow-perturbing element. In all embodiments, the flow perturbing element is adapted to bring about mixing of the sample with itself upstream of the second sample space. Thereby a pristine sample may be prepared in the second sample space, independent of the flow history upstream thereof during fluid handling in the sample chamber. By presenting a pristine sample in the second sample space it may be ensured that an analyte concentration in an interface layer of the fluid sample adjacent to the sensor surface of the porous sensor element is representative of the entire fluid sample. Thereby, a reliable and reproducible parameter measurement can be obtained from the sub-sample extracted from that interface layer into the pores of the porous membrane.

In some embodiments, the flow-perturbing element may be configured to force a transition in flow conditions, such as from laminar to turbulent or similarly perturbed flow conditions, in a fluid that is flown through the sample chamber in a direction from the inlet to the outlet.

In some embodiments, the flow-perturbing element is configured to force a transition in flow conditions, so as to bring about a laminar stirring of a fluid sample that is flown through the sample chamber in a direction from the inlet to the outlet. Also here, the flow-perturbing element enables a mixing of the fluid with itself downstream of the first sample space of the sample chamber, and at least upstream of the second sample space of the same sample chamber. However, in these embodiments the flow perturbing element is now configured so as to maintain a laminar flow regime throughout the entire sample chamber for typical flow rates applied during fluid handling of at least the complex fluid sample to be measured. This embodiment of the sensor assembly is particularly useful for use in measurements on whole blood samples including measurements of the hemolysis of a patient. Thereby, excessive shear forces on the particulate phase of a whole blood sample can be avoided, which otherwise might lead to undesired hemolysis that would render a hemolysis measurement useless. By configuring the flow perturbation element such that the induced flow perturbation causes laminar mixing, it can be ensured that a representative sample is presented for measurements also at the interface on the sensor surface in the second sample space, independent of the flow history through the first sample space upstream of the second sample space during filling of the sample chamber, without the risk of damaging the fluid sample to be analyzed by excessive shear forces within the fluid sample during fluid handling in the sample chamber.

Advantageously, the flow-perturbing element may be arranged in or at the upstream end of a feed channel connecting the first sample space with the second sample space. Advantageously, the flow-perturbing element arranged in or at the upstream end of such a feed channel is configured to force a transition in the flow pattern, such as from a laminar flow received from the first sample space to a turbulent flow or similarly perturbed flow pattern downstream thereof. More particularly, the flow-perturbing element is in some embodiments adapted to induce stirring in a fluid that is flown through the sample chamber in a direction from the inlet to the outlet, at least within the feed channel connecting the first sample space with the second sample space. Thereby, the flow-perturbing element enables mixing of a fluid with itself after having passed the first sample space, and at least before entering the second sample space. Thereby the likelihood of a representative fluid sample interface being reliably presented at the porous membrane sensor surface in the second sample space is increased.

Advantageously, the flow perturbation in a fluid handling flow through the sample chamber is local and upstream (possibly immediately upstream) of the second sample space. The flow-perturbing element is thus configured to cause a local flow perturbation and, in some embodiments, stirring a fluid flown there through upstream (possibly immediately upstream) of the second sample space, while flow conditions for fluid handling in the second sample space are again laminar.

Operating the sensor assembly typically includes steps of filling the sample chamber with a fluid by flowing an amount of the fluid from the inlet through the sample chamber to the outlet, stopping the flow when filling is completed, and performing measurements on the fluid sample thus presented in the sample chamber.

The analyte is extracted from the fluid sample into the porous membrane by means of diffusion. Applying a suitable probing mechanism, such as the below described optical probing, the analyte may then be detected. The term "detection" as used herein is considered to include the mere qualitative detection of the presence of a given analyte and/or a quantitative measurement, such as a measurement for determining the concentration of the analyte in the complex fluid sample. The pores of the porous membrane are in diffusive fluid communication with the sample chamber. The pores are configured with regard to the analyte for diffusive fluid communication between a fluid in the pores and the fluid sample in the second sample space of the sample chamber. The pores are thus configured for exchanging the analyte with the continuous fraction of the complex fluid sample in the sample chamber through diffusive transport while preventing the much larger particles of the discontinuous phase of the complex fluid sample to enter the pores.

As mentioned, operating a measurement device for performing measurements on a given fluid sample in a sample assembly according embodiments of the invention typically include steps of fluid handling, such as steps of rinsing, i.e. flowing a rinsing fluid through the sample chamber in a flow direction from the inlet to the outlet so as to remove any previously presented fluid sample and any contaminants, e.g. stemming from previously presented fluid samples, from the sample chamber. Furthermore, operating a measurement device using the sensor assembly typically includes steps of calibrating the device by means of measurements performed on calibration fluids presented in the sample chamber. Operation of the sample assembly therefore includes frequent fluid handling operations, such as filling, discharging, and refilling of the sample chamber by flowing different fluids through the sample chamber in a direction of flow from the inlet to the outlet.

Most preferably, the first and/or the second sample space are configured for laminar flow during fluid handling in the sensor assembly. Laminar flow through a sample chamber for detecting one or more analytes is normally desirable, in order to achieve a reliable and reproducible fluid replacement performance. Therefore, it is also desirable to maintain laminar flow conditions during fluid handing in the sensor assembly. In contrast to this, however, the flow-perturbing element brings about a mixing of the fluid sample with itself, immediately upstream of the second sample space. Preferably, the flow perturbation is localized to a portion of the sample chamber between the first and second sample spaces, i.e. downstream of the first sample space and upstream of the second sample space. Furthermore, laminar flow conditions are preferably maintained during fluid handing in the sensor assembly in the first sample space, while at the same time maintaining a flow perturbation at the flow-perturbing element, downstream of the first sample space. Furthermore, laminar flow conditions are preferably also maintained during fluid handing in the sensor assembly in the second sample space, while at the same time maintaining a flow perturbation localized at the flow-perturbing element, upstream of the second sample space.

By providing a flow-perturbing element arranged upstream of the second sample space, between the first sample space and the second sample space, erratic depletion measurement artefacts originating in the boundary layer of the fluid sample contacting the porous membrane sensor surface in the second sample space are more and more reduced, or even avoided. For example, effects of border layer depletion and cross-contamination of the fluid sample in a very thin border layer close to the channel walls, e.g. due to miniscule remainders of a previously presented fluid sticking to parts of the chamber walls and/or the porous membrane sensor surface facing the second sample space may be reduced or even obviated thereby.

Further, according to some embodiments of the sensor assembly, the porous membrane sensor element is configured for detecting a high molecular weight analyte.

In the context of the present application, the term "high molecular weight" refers to a molecular weight of 10 000 Da or above, such as 30 000 Da or above, or such as 50 000 Da or above. An example of detecting high molecular weight analytes in a continuous fraction of a complex fluid is detecting hemolysis in a whole blood sample.

A particular merit of the invention is to realize that the diffusive transport close to the chamber wall comprising the sensor surface is of particular importance when analyzing a complex fluid sample for high molecular weight components present in a continuous fraction of the complex fluid. Without being bound by theory, one reason for this surprising delicacy of measurements when analyzing for high molecular weight components in a complex fluid may reside in a "labyrinth effect" impeding the diffusion of such high molecular weight components in the continuous fraction, through a "labyrinth" formed by large particles of the discontinuous fraction, and towards the chamber walls. Due to this labyrinth effect, the diffusivity of high molecular weight components, through particles of the discontinuous phase may be lowered to such a degree that analytes for analysis in the porous membrane are essentially drawn from a border layer of the continuous fraction, contacting the sensor surface, since diffusion of analyte to the sensor surface into the pores from deeper regions of the complex fluid sample that are further away from the sensor surface may be efficiently blocked by the discontinuous fraction.

This issue is at least reduced, if not obviated by providing a flow-perturbing element upstream of the second sample space. By means of the flow-perturbing element, the complex fluid sample is stirred up immediately upstream of the second sample space, and a complex fluid sample with a representative concentration of the high molecular weight analyte in the border layer for contacting the porous membrane sensor surface is provided. Without being bound by theory, this may be attributed to a reduction in the apparent diffusive depletion for high molecular weight analyte components in a very thin border layer of the continuous fraction of the complex fluid sample, as otherwise may occur, due to miniscule remainders of previously presented fluid samples, rinsing fluids, and/or calibration fluids sticking to the chamber walls upstream of the second sample space, all the way from the inlet. This leads to more reliable and reproducible measurements when analyzing for high molecular weight components in the continuous fraction of the complex fluid.

Further, according to some embodiments of the sensor assembly, the first sample space comprises one or more further sensor elements for detecting respective further analytes. Thereby, the sensor assembly is adapted for simultaneous analysis with respect to multiple analytes, including both the analyte detectable by the porous membrane sensor element in the second sample chamber and the further analytes detectable by the one or more further sensor elements arranged in the first sample space. By arranging the further sensor elements in the first sample space upstream of the flow-perturbing element, this is achieved without interfering with the measurement quality for the analyte detected by the porous membrane sensor element arranged in the second sample space, downstream of the flow-perturbing element.

Further, according to some embodiments of the sensor assembly, the flow-perturbing element is formed as an abrupt change in the sample chamber geometry. For example, the flow-perturbing element is configured to bring about the flow perturbation by an abrupt change in the direction of the flow through the sample chamber from the inlet to the outlet. According to some embodiments, the sample chamber may be a channel extending from the inlet to the outlet comprising a sharp cornered bend, wherein the second sample space is arranged downstream of the sharp cornered bend. According to advantageous embodiments, a bend may be considered as a sharp cornered bend if a center line of the channel following the bend has a radius of curvature that is less than a width of the channel at the bend. According to advantageous embodiments, a bend may also be considered as a sharp cornered bend if a smallest radius of curvature in a direction following the principal direction of the sample chamber from the inlet to the outlet has a radius of curvature that is less than a width of the channel at the bend. A sharp cornered bend or similar abrupt change in the direction of the channel has the advantage over other flow-perturbing elements that dead spaces in the wake of the flow-perturbing element can be avoided more easily. Such dead spaces are undesired as they might attract bubbles, droplets, and similar reminiscent contaminants that are difficult to rinse out and may contaminate subsequent samples, thus corrupting measurements performed on such subsequent samples.

Further, according to some embodiments of the sensor assembly, the flow-perturbing element is formed as a connection nozzle connecting a feed channel of the second sample space to a downstream end of the first sample space. Thereby an efficient and simple implementation of an abrupt change in the direction of the channel can be achieved.

Further, according to some embodiments of the sensor assembly, the flow-perturbing element is formed as a connection nozzle arranged at an angle with respect to a principal axis of a sample channel forming the first sample space, wherein the angle is at least 30 degrees, at least 40 degrees, at least 50 degrees, at least 70 degrees, or typically about 90 degrees with respect to said principal axis. Thereby, a further, efficient and simple implementation of an abrupt change in the direction of the channel can be achieved.

Further, according to some embodiments of the sensor assembly, the flow-perturbing element is located immediately upstream of the second sample space at a distance from an entry orifice of the second sample space of at least 0.3 mm, 0.5 mm, 1 mm and/or up to 3 mm, up to 5 mm, or up to 10 mm. Thereby, a flow perturbation in the immediate vicinity upstream of the second sample space is achieved. Advantageously according to some embodiments, the first sample space is a formed as a channel having a top wall, a bottom wall, and sidewalls connecting the top and bottom walls, thereby defining an essentially rectangular cross-section as seen in a cut-plane perpendicular to the principal direction of the first sample space from the inlet to the outlet. Advantageously, the rectangular cross-section of the first sample space has a width as seen in a transverse direction parallel to the top and bottom walls in the range of a few millimeters, such as up to 10 mm, up to 5 mm, or up to 3 mm, and at least 1 mm, or at least 2 mm, such as about 2.4 mm; and a height as seen in a direction perpendicular to the top and bottom walls in the submillimeter range, such as less than 1 mm, less than 0.8 mm, less than 0.5 mm, and at least 0.1 mm, or at least 0.2 mm, or at least 0.3 mm, such as about 0.4 mm. Further, advantageously, the flow-perturbing element is a nozzle forming a T-shaped junction or an L-shaped junction at the downstream end of the first sample space. Preferably, the nozzle connects to one of the top and bottom walls of the first sample space, at the downstream end thereof. Further, according to some embodiments of the sensor assembly, the sensor surface is planar.

Further, according to some embodiments of the sensor assembly, the sensor surface is arranged parallel to the direction of flow from the inlet to the outlet for fluid handling in the second sample space of the sample chamber. Thereby an efficient contacting of the sensor surface with a sample surface is achieved. Furthermore, a smooth and efficient replacement of fluids contacting the sensor surface during fluid handling operations is achieved. Furthermore, cross-contamination may thereby by reduced.

Further, according to some embodiments of the sensor assembly, the second sample space has a cylindrical shape defined by a top wall, a bottom wall opposite to the top wall, and a circumferential wall connecting the top and bottom walls; wherein a feed orifice is arranged at an at an upstream end of the second sample space, i.e. as seen in a direction towards the flow perturbation, towards the first sample chamber, and towards the inlet; and wherein a discharge orifice is arranged at a downstream end thereof, i.e. as seen in a direction towards outlet. Preferably, the porous membrane sensor element is arranged in the top wall. According to some embodiments, the cylindrical shape may have a circular cross-section, or an elliptical cross-section as seen in a cut-plane parallel to the sensor surface.

Further, according to some embodiments of the sensor assembly, the feed and discharge orifices are arranged in the circumferential wall. Preferably, the feed and discharge orifices are arranged opposite to each other. Thereby, a simple flow pattern for flow through the second sample space is achieved when performing fluid handling operations. Consequently, a further smooth and efficient replacement of fluids contacting the sensor surface during fluid handling operations is achieved. Furthermore, cross-contamination may thereby by reduced.

Further, according to some embodiments of the sensor assembly, a height of the second sample space as seen in a direction is from the top wall to the bottom wall is less than one half, or less than one third, or less than one fifth, or even less than tenth of a transverse dimension of the second sample space. Thereby, a smaller volume of the fluid sample is required, without compromising the quality of the measurement performed in the porous membrane sensor element. This feature further benefits from the inventive insight that the measurements in the porous membrane sensor element rely on diffusive exchange of the analyte with a relatively thin border layer of the complex fluid sample contacting the sensor surface, in particular with regard to high molecular weight analytes.

Further, according to some embodiments of the sensor assembly, the bottom wall is curved to reduce the distance of the bottom wall from the top wall in a center portion of the second sample space, as compared to a peripheral portion thereof. Preferably, the porous membrane sensor element is arranged in the top wall. Preferably, in this embodiment, the porous membrane sensor element is planar. The bottom wall may be curved to bulge at least along a direction from the feed orifice to the discharge orifice towards the top wall, such that the bottom wall is closer to the top wall in a center portion than at the feed/discharge orifices. Preferably, the bulging is gradual to avoid dead spaces that are difficult to clear out when switching between different fluids presented in the sample chamber (e.g. rinse/calibration ⇔ test sample). Thereby a further reduced sample volume may be achieved without compromising the measurement quality, while furthermore achieving a smooth flow pattern for efficient fluid handling operations, thus further reducing the risk of any of the above-mentioned complications during fluid handling operations.

Further, according to some embodiments of the sensor assembly, the porous membrane sensor element is configured for detecting the analyte by optical probing. Thereby a highly sensitive probing mechanism is provided.

The terms "optical" and "light" and related terms generally refer to electromagnetic radiation in the visible, infrared, and ultraviolet spectral ranges: the term "visible" typically refers to electromagnetic radiation with wavelengths in the range of 400 nm-700 nm; the term "infrared" broadly refers to electromagnetic radiation with wavelengths in the range of 700 nm-1 mm, with typical subranges of about 700 nm-3 μm in the "near-infrared", 3 μm-50 μm in the "mid-infrared", and 50 μm-1 mm in the "far-infrared"; the term "ultraviolet" or "UV" broadly refers to electromagnetic radiation with wavelengths in the range of 10 nm-400 nm, with typical subranges of 300 nm-400 nm in the "near ultraviolet", 200 nm-300 nm in the "middle ultraviolet", and 122 nm-200 nm in the "far ultraviolet". The skilled person will understand that the usefulness of the mentioned spectral ranges for a given sensor element, and in particular for a given translucent membrane material, will depend on the compatibility of spectral ranges and materials for propagating input and output light through these materials.

Further, according to some embodiments of the sensor assembly, the porous membrane is a translucent membrane, wherein the porous membrane sensor further comprises: a reflective layer arranged at the front side of the translucent membrane; an optical input port 220 connected to a back side of the translucent membrane, the backside facing away from the front side, optical input port 220 being adapted for feeding probing light to the probing region of the translucent membrane through the back side; and an optical output port 225 connected to the back side of the translucent membrane, the optical output port 225 being adapted for collecting an optical response from the translucent membrane through the backside.

The term "translucent" refers to a material's property of allowing light to pass through. The term "transparent" refers to the property of a material of allowing light to pass through the material without being scattered. The term "transparent" is thus considered a sub-set to the term "translucent".

The optical input port is configured for feeding probing light through the backside into the translucent membrane. The optical output port is configured for collecting an optical response to the probing light from the translucent membrane through the backside. By both injecting the probing light and collecting the optical response from the back side of the translucent membrane, a compact design is achieved allowing for the integration of the sensor element in a miniaturized sample assembly with a very small sample chamber, which is designed for analyzing very small amounts of a sample fluid.

The back side of the translucent membrane is typically parallel to the front side; an additional transparent backing may be applied to the back side in order to provide a mechanical support for stiffening/reinforcing the translucent membrane from the back side; The backing may be a transparent padding filling voids between the translucent membrane and further optical components of the sensor element, such as the input port, and/or the output port. The sensor element is typically held together in a mechanical mount, such as in a sensor element housing. Any void between the backside of the translucent membrane and any of the further optical components may be filled out with a transparent padding component. Preferably, according to some embodiments, a transparent padding is refractive index matched with the translucent membrane to within tolerances, such as to within 5%, preferably within 2%, and most preferably to within 1%.

As mentioned above, the porous membrane sensor element has a sensor surface for contacting a fluid to be analyzed. The sensor surface is formed at the front side of the translucent membrane and the reflecting layer applied to the front side. The translucent membrane contains small pores, preferably dead end pores, extending from the front side, through the reflective layer into the translucent membrane. Each of the small pores has an opening through which it can communicate with a fluid space at the front side of the translucent membrane. The pores thus penetrate the reflecting layer to allow for fluid communication between the pores and the fluid space. The pores extend from the respective opening at the front side into the translucent membrane in a direction towards the backside. The pores are preferably "dead end" meaning that the pores end within the translucent membrane. The dead end pores do not continue all the way through the translucent membrane to the backside or to any common reservoir or recipient inside the membrane. The pores are only in fluid communication with the fluid space at the front side of the translucent membrane. Note that in some embodiments, the dead end pores can be crisscrossing and at least some of the pores may thus be connected to each other forming an X-shape, a Y-shape, a V-shape, or similar interconnected shapes. Such a configuration is equally considered as dead end, since the pores are only filled from the front side and no significant net mass transport passing through the pores occurs under operation, even if they cross each other.

The translucent membrane may be made from transparent polymer membranes with pores fabricated therein using, for example, so-called track-etching techniques as disclosed in the co-pending international patent applications, WO 2017/085162 A1 and WO 2017/085180 A1, which are hereby incorporated by reference.

The pores form vials/cuvettes for selectively receiving an analyte from a first fraction of the fluid, in particular via diffusion/diffusive transport, whereas a particulate fraction is effectively prevented from entering the pores. These vials/cuvettes are placed at least in a probing region for efficient interaction of probing light with the analyte. The openings of the pores are dimensioned such that a particulate fraction of the fluid to be analyzed is kept outside the pores, while allowing an analyte from a further fraction, e.g. a continuous fraction, to enter through the pores into the translucent membrane, so that the probing light injected from the input port can interact with the analyte and thus detect the analyte by optical probing. By appropriately dimensioning the opening of the pores at the front side it is possible to prevent e.g. red blood cells of a whole blood sample at the sensor surface from entering the pores, while allowing relevant components in the plasma fraction of the whole blood sample to enter the pores, wherein relevant components are substances present in the plasma fraction of the whole blood sample (or more generally in the relevant fraction of the fluid sample) and that are to be measured/detected using the sensor.

By this configuration, it is achieved that a small, but representative analyte fraction is gently extracted from the complex fluid and efficiently exposed to the probing light in the probing region with a high degree of overlap. This separation is achieved in a particularly simple and fast manner, since the probing region is arranged directly at the surface of the translucent membrane with the pores penetrating directly into the translucent membrane, and with a relatively short distance from their respective openings at the sensor surface to the location of probing, thus facilitating a particularly rapid diffusive exchange of the sample.

Typical cross-sectional dimensions of the pores are in the micron and sub-micron range down to about 100 nm. Analyte transport into and out of the pores is achieved by diffusion. For efficient operation, the pores are filled with a priming fluid, which preferably is filled into the pores in a priming step, e.g. prior to performing the first detection measurement. The priming fluid may not affect the fluid to be analyzed. The priming fluid thus has to be compatible with the fluid to be analyzed. Advantageously, the priming fluid may be a rinsing fluid, such as an aqueous buffer solution, which may also be used for rinsing a sample chamber during filling, emptying and re-filling procedures for replacing samples of a fluid to be analyzed. The rinsing fluid may also be a reference fluid or a calibration fluid.

Advantageously according to some embodiments, the pores are filled with a liquid. Priming the pores with a known liquid allows for extracting a subsample representative of the relevant components in the fluid to be analyzed into the pores by diffusion alone. This provides for a fast, efficient and well-controlled exchange of the analyte via the pores into and out of the optical probing region. Advantageously according to some embodiments, the liquid is an aqueous solution. This is particularly useful for the detection of water-soluble analytes. Alternatively, it is conceivable that the pores are filled with a non-aqueous liquid, which e.g. is particularly useful when the fluid to be analyzed is also a non-aqueous liquid.

Under operation, the front side of the translucent membrane may be contacted with e.g. a whole blood sample or a fluid. The small pores in the translucent membrane communicate with the whole blood sample or fluid through the openings in the front side. The pore openings are dimensioned to extract selectively a sub-sample of the plasma phase of the whole blood sample or to extract a sub-sample of the fluid including the analyte. No red blood cells can enter the pores through the openings on the front side of the translucent membrane. Nothing larger than the pore diameter can enter the pores, which excludes e.g. any debris included in the fluid. As mentioned, the pores are preferably dead end, only communicating with the front side of the translucent membrane, i.e. the sub-sample is extracted for optical probing inside the pores and after the measurement discharged again through the same openings in the front side of the translucent membrane. The sub-sample volume corresponds to the total internal volume of the pores. No filtration and net mass transport of any filtrate occurs through the pore-containing layer—neither into any common filtrate recipient nor to any filtrate outlet. The optical detection will then be performed only on the sub-sample contained in the pores. The reflective layer optically separates the optical probing region in the translucent membrane from the fluid space containing the whole blood sample or the fluid. By optically separating the probing region from the fluid space, any contribution of the intact red blood cells of the whole blood sample or of the debris in the fluid to the probed signal can be effectively suppressed. The measurement is thus specific to the content of analyte in the fluid.

The small sub-sample with a representative content of the relevant components may be transferred to the pores in any suitable manner. The small dead end pores allow for a very efficient and fast extraction of the sub-sample for optical probing from a whole blood sample or a fluid through the openings in the front side by means of capillary forces and/or diffusion. In a typical operation mode, the front side surface of the translucent membrane is contacted by a rinsing fluid prior to contacting the front side with a whole blood sample or fluid that is to be analyzed. Thereby, the pores are 'primed' with a prefill of a liquid that is compatible with the whole blood sample or the fluid, and in particular a liquid that is compatible with the plasma phase if the fluid is whole blood, such as an aqueous solution commonly used for rinse, calibration and/or quality control purposes in blood analyzers. Typical rinse liquids used for e.g. washout in whole blood analyzer systems may be used as such a liquid. Rinse liquids are aqueous solutions comprising $K^+$, $Na^+$, $Cl^-$, $Ca^{2+}$, $O_2$, pH, $CO_2$, and $HCO^{3-}$ in concentrations corresponding to human plasma. When the whole blood sample or fluid is then brought in contact with the front side surface that is primed with a plasma compatible liquid/fluid compatible liquid, a representative sub-sample of components in the plasma phase of the whole blood sample or of the fluid is extracted and transferred in a very efficient and gentle manner by means of diffusion of the relevant components into the prefilled pore. In particular, any concentration gradient in the content of the analyte between the fluid and the reference liquid in the pores drives a diffusive transfer, thereby producing in the pores a sub-sample with an analyte concentration representative of the analyte concentration in the fluid.

The sub-sample volume corresponds to the total internal volume of the pores. No filtration and net mass transport of any filtrate occurs through the pore-containing layer during measurement—neither into any common filtrate recipient nor to any filtrate outlet. The optical detection is then performed only on the sub-sample contained in the pores. The confinement of the input light to the translucent membrane optically separates optical probing from the fluid space containing the whole blood sample or the fluid. By optically separating the optical probing from the fluid space, contributions of the intact red blood cells of the whole blood sample or of the debris in the fluid to the probed signal can be effectively suppressed. The measurement is thus specific to the content of analyte in the fluid.

The content of the pores can conveniently be probed optically from the back side of the translucent membrane, or more generally, from the side of the reflective layer facing towards the translucent membrane, wherein the reflective layer at the front side optically separates an optical probing region comprising the pores from the fluid contacting the front side of the translucent membrane. The reflective layer is adapted to reflect light reaching the reflective layer from directions from the backside of the translucent membrane, thereby preventing probing light from reaching and interacting with the fluid at the front side of the translucent membrane. The optical probing is thus selectively performed only on the sub-sample inside the pores.

Further, according to some embodiments, the sensor assembly further comprises a light source connected to the optical input port, wherein the light source is configured for emitting probing radiation. Further according to some embodiments, the sensor assembly further comprises a detector connected to the optical output port, wherein the detector is configured for detecting light emerging from the probing region in response to an illumination of the probing region through the input port by the light source, and wherein the detector is adapted to generate a signal representative of the detected light. The light source may be any light source that transmits light in a region where the analyte in the pores absorb light or otherwise provides an optically stimulated response in order for the system to work. Due to their properties with respect to size, weight, efficiency etc. light emitting diodes are preferred for embodiments intended for miniaturization and/or integration in an assembly. The detector may be any optical detection set-up suited for detecting the optical response received from the optical output port, and for analyzing that optical response in order to generate an output signal indicative of the analyte to be detected. Advantageously according to one embodiment, the detector may include a spectrophotometer and an optical probing device is configured for the spectrophotometric analysis of the light emerging from the probing region. This allows for resolving the spectral signature of one or more relevant components in the light emerging from the sub-sample in the probing region. For purposes of miniaturization and compactness, e.g. in the context of point-of-care set-ups, the detector may include a photodiode or a spectrometer that is able to detect the absorption in the entire spectrum. Alternatively, an array or diodes may be used, where each diode emits light at different wavelengths, and a photodiode is used as a detector. The diodes may be multiplexed to emit light in different intervals. The absorption is then found by comparing the light emitted from a diode in that particular interval compared with the light detected by the photodiode.

The following embodiments disclose advantageous rules and ranges for dimensioning the pores, in particular for use in a sensor element in the context of optically probing body fluids.

Further, according to some embodiments of the sensor element, a cross-sectional dimension of the openings of the pores is about 1 µm or less, about 800 nm or less, preferably about 500 nm or less, or even about 400 nm or less. The cross-sectional dimension of the pore openings is preferably adapted so as to balance size selectivity (smaller pore opening diameter) against a rapid exchange of sub-sample/analyte (larger pore opening diameter)—depending on the application. The given values are, for example, particularly useful for the analysis of body fluids, such as whole blood with an analyte in the plasma fraction.

Further, according to some embodiments of the sensor element, a cross-sectional dimension of the openings of the pores is at least 200 nm. The cross-sectional dimension of the pore openings is preferably adapted so as to balance size selectivity (smaller pore opening diameter) against a rapid exchange of sub-sample/analyte (larger pore opening diameter)—depending on the application. The values of the recited range are, for example, particularly useful for the analysis of body fluids, such as whole blood with an analyte in the plasma fraction.

Further, according to some embodiments of the sensor element, a length of the pores in an axial direction along the pores is less than 100 µm, less than 50 µm, and preferably less than 30 µm. The length of the pores is preferably adapted so as to balance a desire to provide an increased sample volume (longer pore length) for interaction with the optical probing field in the probing region against rapid exchange of sample/analyte (shorter pore length)—depending on the application. The given values are particularly useful for the analysis of body fluids, such as whole blood with an analyte in the plasma fraction of the whole blood sample.

Further, according to some embodiments of the sensor element, a length of the pores in an axial direction along the pores is at least 1 µm, at least 2 µm, at least 5 µm, and preferably at least 10 µm. The length of the pores is preferably adapted so as to balance a desire to provide an increased sample volume (longer pore length) for interaction with the optical probing field in the probing region against rapid exchange of sample/analyte (shorter pore length)—depending on the application. The given values are particularly useful for the analysis of body fluids, such as whole blood with an analyte in the plasma fraction of the whole blood sample.

Further, according to some embodiments of the sensor element, the pores are straight. Straight-shaped pores facilitate an effective transport through the length of the pore, thereby achieving a fast sub-sample/analyte exchange.

Further, according to some embodiments of the sensor element, the pores are track-etched pores formed by exposing the translucent membrane to a directional ion bombardment followed by chemical etching. Track etching is particularly well suited for forming straight-shaped and narrow, yet deep pores of e.g. the above-mentioned dimensions. The pores may be formed in a unidirectional arrangement resulting, e.g. from a single directional ion bombardment exposure. Alternatively, the pores may be formed in a multidirectional arrangement by providing multiple directional ion bombardment exposures from different directions. The pore arrangements may thus e.g. be created/defined by one or more directional ion-bombardment exposures prior to performing the etching steps.

A suitable translucent membrane may be produced e.g. from transparent polymer membranes with so-called track-etched pores, similar to those available from the company IT4IP (IT4IP S.A./avenue Jean-Etienne Lenoir 1/1348 Louvain-la-Neuve/Belgium) with the modification that the pores are closed at one end. Through-going pores in the membranes may be closed e.g. by laminating a backing sheet to the backside of the porous membrane, or by decelerating the ions such that the ion-bombardment tracks, and thus the pores etched following these tracks, stop within the transparent polymer membrane to form dead end pores. The membrane is typically backed by a stiff transparent element to provide adequate mechanical strength to the translucent membrane.

The translucent membrane should preferably be made of a material that does not absorb light and at the same time it should be possible to produce the dead end pores in the material e.g. by track etching the material. A material that is suitable for this is, for example, polyethylene terephthalate (PET or PETE) or an analogue of PET (polyethylene terephthalate polyester (PETP or PET-P)) or a polycarbonate (PC). The translucent membrane may comprise a hydrophilic coating of e.g. polyethylene glycol (PEG) to increase the diffusion into the pores. The hydrophilic coating may be chosen so as to configure the sensor element for a certain mode of operation of the sensor element. In some modes of operation, the sensor element will never dry out, once it is in use and it therefore only needs to be hydrophilic at startup. For other modes of operation of the sensor element, a coating is applied that permanently keeps up the hydrophilicity throughout the entire lifetime of the sensor element. This allows for an operation mode where the sensor element is allowed to dry out between subsequent uses, yet maintaining a fast sub-sample extraction from a liquid sample presented at the sensor surface. Consequently, a fast measurement turn-around from contacting the sensor surface with a liquid sample to obtaining an optical probing result can be achieved even though the sensor element is allowed to dry out between uses.

Advantageously according to some embodiments of the sensor element, a porosity of a given volume of the translucent membrane comprising pores, at least within the probing region, is between 50% and 5% by volume, between 30% and 10% by volume, or about 15% by volume. The porosity may be characterized in terms of the volume of the voids created in the translucent membrane by the pores, i.e. the pore volume, wherein the pore volume is referred to the volume of the translucent membrane penetrated by the pores. This volume is here defined as the volume between the front side area over which the pores are distributed and the identical parallel area shifted into the translucent membrane by the maximum depth of penetration of the pores into the translucent membrane as seen in a vertical direction perpendicular to the sensor surface.

In addition thereto, the porosity may be further characterized in terms of the integrated pore volume, which is equal to the sub-sample volume that is available for optical probing. The pore volume may conveniently be expressed as an equivalent pore volume depth DELTA, which is the pore volume referred to the corresponding front side area over which the pore openings are distributed. Accordingly, the porosity of the translucent membrane can be converted into an equivalent pore volume depth DELTA as follows. The pores having an opening within a given front side area a have a total pore volume V. The equivalent pore volume depth is then calculated as the total pore volume divided by the given front side area: DELTA=V/A.

Advantageously according to some embodiments, an equivalent pore volume depth DELTA is less than 20 µm, or less than 15 µm, or less than 10 µm, or in the range from 3 µm to 5 µm, wherein the equivalent pore volume depth DELTA is defined as the total volume of the pores V divided by the front side area A over which the openings of the pores are distributed. Thereby, a small sub-sample with a representative concentration of relevant components is obtained. A small sub-sample volume is desirable to promote a fast sub-sample exchange, thereby reducing response time of the sensor element, and cycle time of measurements using the sensor element. A small subsample volume is further desirable in order to avoid effects of depletion of boundary layers of a plasma fraction in a whole blood sample close to the front side of the translucent membrane. Such depletion effect may otherwise occur in small, still standing samples, where e.g. red blood cells may obstruct an efficient diffusive exchange of relevant components from the volume of the whole blood sample towards the boundary layer at the front side of the translucent membrane, if the equivalent pore volume depth exceeds a critical value.

Preferably, an equivalent pore volume depth DELTA is at least 1 µm, alternatively at least 2 µm, or in the range from 3 µm to 5 µm, wherein the equivalent pore volume depth is defined as above. A larger sub-sample volume is desirable to achieve a better signal-to-noise level due to a larger sub-sample volume contributing to the optically probed information on the relevant components in the plasma.

Further according to some embodiments, a useful compromise between reducing response time, reducing cycle time, and/or avoiding depletion effects in small still standing whole blood samples or fluids on the one hand, and a required or desired signal-to-noise ratio on the other hand is found for an equivalent pore volume depth DELTA in the range from 1 µm to 20 µm, preferably in the range from 2 µm to 10 µm or at about 4 µm-5 µm.

Further, according to some embodiments of the sensor element, an inner wall surface of the pores is hydrophilic, e.g. coated with a hydrophilic coating. Thereby, an efficient capillary driven filling of dry pores with liquid is achieved. Furthermore, a hydrophilic coating prevents certain hydrophobic substances, such as hydrophobic dyes, hemoglobin, and other proteins, from depositing inside the pores that would otherwise lead to a gradual fouling of the sensor, which is difficult to wash out with an aqueous solution.

Advantageously according to some embodiments, the reflective layer is made of metal. Such metallic coatings can be applied in a relatively cost-effective, yet well-controlled manner with adequate reflectivity.

Advantageously according to some embodiments, the reflective layer is made of platinum, palladium or an alloy comprising as a principal component platinum or palladium. These materials exhibit a good reflectivity in the spectral range of the electromagnetic spectrum (deep violet to blue) that is relevant for the detection of certain substances, e.g. free hemoglobin, for example by absorbance probing. Furthermore, these materials are biocompatible and do not e.g. introduce artificial hemolysis. Furthermore, these materials are chemically stable in general and in particular in the chemical environment of biological fluids, such as a whole blood sample or any of the previously mentioned body fluids.

Alternatively, according to some embodiments, the reflective layer may be made of silver or aluminum. Further advantageously according to some embodiments, the surfaces of the reflective layer facing towards the sample volume are encapsulated by an additional passivation layer, thereby enhancing the lifetime of the device, in particular when using silver or aluminum as a material for the reflective layer. A suitable passivation may be made of e.g. a thin layer of $SiO_2$, which preferably is made transparent and has to be sufficiently thin so as not to obstruct the opening of the pores. These materials may also provide a good reflectivity in the relevant spectral range (red), are biocompatible and chemically stable in the environment.

Advantageously according to some embodiments, the thickness of the reflective layer is between 10 nm-100 nm depending upon the used metal. Such a layer thickness allows for applying the reflective layer by an evaporation technique without clogging of the openings of the pores at the sensor surface. At the same time, the layer thickness has to be sufficient to provide adequate attenuation of light propagating to the sample volume in order to ensure an enhanced optical separation between the probing region and the sample volume containing the fluid to be analyzed, e.g. a whole blood sample. Preferably, the transmitted light is less than 5%, less than 1% or even less than 0.1% in the spectral range of detection, i.e. in the spectral range from which a signal representative of the relevant component is developed. For example, for measuring hemoglobin in the plasma fraction of a whole blood sample suitable spectral ranges are from 380 nm to 700 nm, from 380 nm to 450 nm, from 400 nm to 430 nm, or at about 416 nm.

According to a yet further aspect of the invention, a method of optically detecting an analyte such as hemoglobin in a fluid is provided. The method implements the steps of providing a fluid sample in a sample chamber and optically probing said fluid sample for an analyte as discussed herein in the disclosure of the sensor assembly and system, and at least achieves the same advantages as discussed with respect to the respective embodiments.

According to some embodiments, a method of detecting an analyte in a complex fluid sample comprises the steps of providing a sensor assembly as disclosed above; contacting the sensor surface of the porous membrane sensor element with a reference liquid so as to fill the pores with the reference liquid; contacting the sensor surface with a sample of the complex fluid to be analyzed; waiting for a diffusion time to allow for diffusion of the analyte in the complex fluid into the pores to stabilize; injecting input light into a probing region from a backside of the porous membrane; collecting light emitted from the pores towards the backside of the porous membrane in response to the input light, thereby optically probing the fluid inside the pores; and, based on the result of the optical probing, establishing an analyte level of the complex fluid. Preferably, the reference liquid is an aqueous solution that is compatible with the fluid, and in particular compatible with the fraction thereof that may enter the pores, such as a liquid for rinse, calibration and/or quality control. Advantageously, an analyte is detected optically in the pores by the color change due to the presence of the analyte in representative amounts in the extracted subsample. Advantageously according to some embodiments, optical probing comprises performing a spectrophotometric analysis of the light emerging from the pores as an optical response to the probing input light. Advantageously according to some embodiments, optical probing is measuring the absorbance. This has the advantage of a relatively simple, yet effective set-up. In particular, the method comprises steps of fluid handling for contacting the sensor surface of the porous membrane sensor element with the complex fluid sample to be analyzed. These steps of fluid handling include flowing the complex fluid to be analyzed through the inlet of the sample chamber, through the first sample space, through a connecting feed channel comprising a flow-perturbing element, the connecting feed channel connecting the first sample space with the second sample space, through the second sample space, and through the outlet, until a predetermined criterion is fulfilled for determining that the sample chamber is filled. The criterion can, e.g. be determined by appropriate fluid interface detectors arranged at the inlet and at the outlet of the sample chamber. Flowing the complex fluid through the sample chamber is performed so as to maintain at least the flow through the first and second sample spaces in a laminar regime, whereas the flow through the connecting channel exhibits a flow perturbation at the flow-perturbing element, immediately upstream of the second sample space.

While the present invention has mainly been described herein with reference to uses in the context of the analysis of blood analysis, the skilled person will understand that the present invention is also useful in other context in an equivalent manner without leaving the scope of the present invention.

For example, the sensor element can be used in a reading device for color producing/consuming assays. Such a device has the advantage that it is not necessary to perform separation steps in order to produce plasma before the assay. By way of example, the following types of assays may be performed with a device comprising a sensor element according to embodiments of the invention: sandwich assays, where the receptor ligand could be bound inside the membrane channels; Assays where one part is bound in the pores, e.g. Bromocresol Green Albumin assay, which use Bromocresol Green (BCG), to form a colored complex specifically with albumin. The intensity of the color, measured at 620 nm, is directly proportional to the albumin concentration in the fluid; Enzyme activity assays as e.g. the aspartate aminotransferase (AST) activity assay kit, where the transfer of an amino group from aspartate to α-ketoglutarate results in the generation of glutamate, resulting in the production of a colorimetric (450 nm) product proportional to the AST enzymatic activity present.

The sensor element may also be used in non-medical applications, such as monitoring tasks for beer brewing, wastewater analysis, food testing and in dye production. In beer brewing a precise color is desired. The sensor element could be used to determine whether or not the beer has the desired color or not by measuring on the liquid and compare the reading with a liquid of correct color. Wastewater could be analyzed for presence or absence of a component. In food testing, liquids such as milk, juices and other slurries, the sensor element could be used for analysis for presence or absence of a constituent or analyte. The sensor element could further be useful in the production of certain chemicals, e.g. in the dye industry, to obtain metrics during the production of a desired color, a desired content or other chemical property of the product.

Advantageously according to some embodiments, the sensor element, or a blood analysis system comprising such a sensor element, further comprises a processor configured for comparing the signal generated by the detector with a predetermined calibration reference to develop a quantitative measure of the analyte level in the fluid. Further, advantageously according to some embodiments, the calibration reference is obtained on a dye-based calibration solution, such as an aqueous solution comprising tartrazine dye. Preferably, the dye-based aqueous solution is prepared from a typical rinse liquid with the addition of the calibration dye, such as tartrazine.

BRIEF DESCRIPTION OF THE DRAWINGS

Preferred embodiments of the invention will be described in more detail in connection with the appended drawings, which show in FIG. 1 a diagram of a liquid sample analyzer comprising a sensor assembly according to one embodiment of the invention.

DETAILED DESCRIPTION

Figure 1:
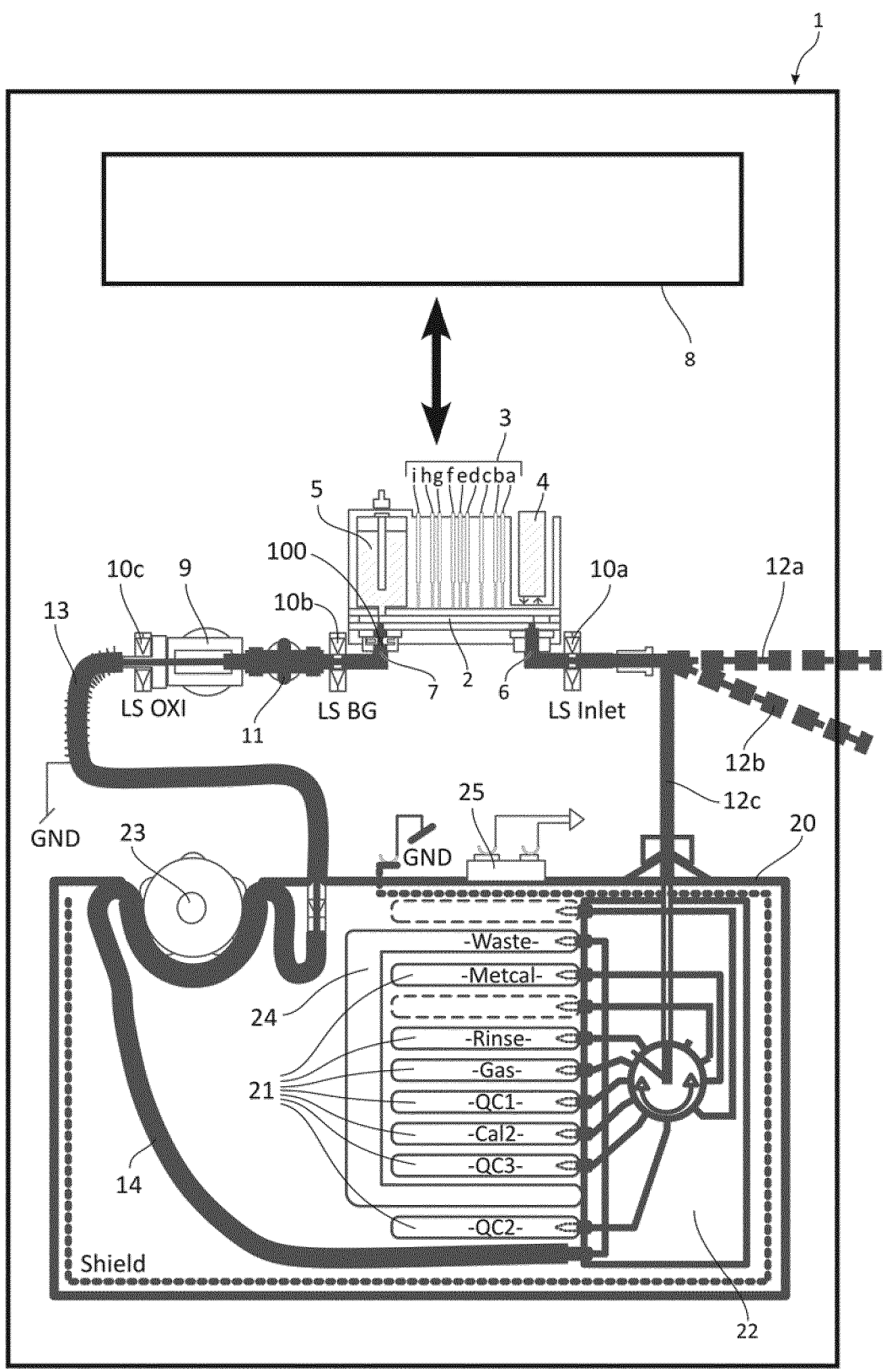
Figure 2:
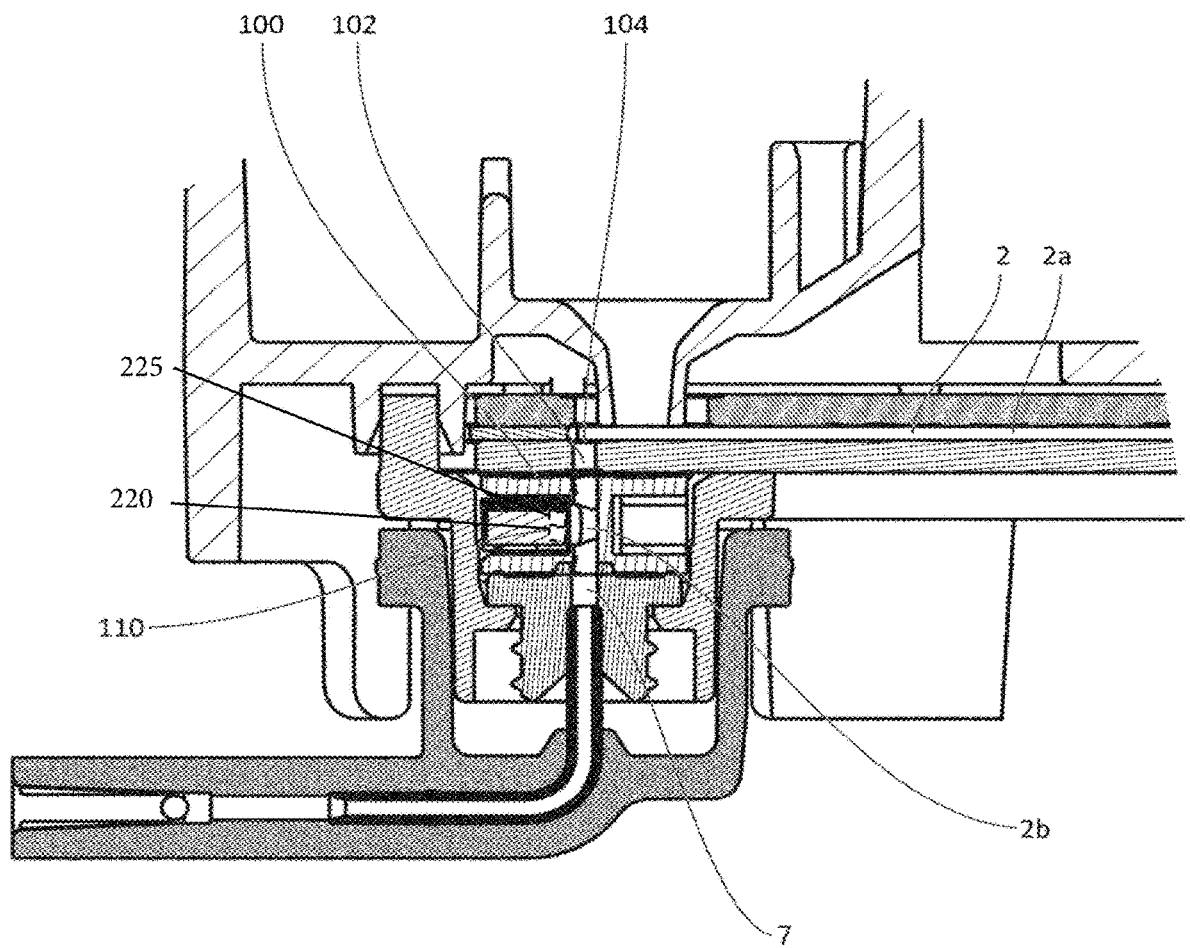
FIG. 2 schematically, a cross-sectional detail of a sensor assembly according to one embodiment.

Referring to FIGS. 1 and 2 in the following, an embodiment of a sensor assembly is described in relation to its operation in a liquid sample analyzer.

FIG. 1 shows schematically a liquid sample analyzer 1 with an analyzer part having a signal processor 8, one or more analyte sensors 3(a-i), 4, a sample chamber 2, and fluid handling infrastructure 20. For performing measurements, the user may provide a liquid sample at an input port 12a/b of the analyzer 1. The liquid sample is transferred through an inlet port 6 to a first sample space 2a of the sample chamber 2, the first sample space 2a comprising a plurality of analyte sensors 3, 4. The analyte sensors 3, 4 are arranged to provide essentially simultaneous measurements on analyte parameters in a complex liquid sample, e.g. a whole blood sample, as also mentioned above. Preferably, the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 B1. The present embodiment differs from this known assembly by the addition of a porous membrane sensor element 100, here arranged at the downstream end of the sample chamber 2. Following pre-programmed instructions loaded in a signal processor 8 and/or user input, measurements are performed using the analyte sensors 3, 4. The analyte sensors 3, 4 generate signals that are representative of a physical parameter for the respective analyte and provide the signals to the signal processor 8 of the analyzer part. The signal processor 8 is adapted to receive and process signals from the analyte sensors 3, 4, and present the processed signals as output to a user or to a subsequent/further data analysis. After measurement, the liquid sample is discharged, and the sample chamber is prepared for the next measurement.

The embodiment of the analyzer shown in FIG. 1 is particularly adapted for the measurement of blood parameters, and further comprises an optional oxygenation measurement device 9 downstream of the sensor assembly. Performing the measurements, calibration tasks, and quality control procedures thus typically involves the loading, unloading, rinsing, cleaning and re-loading of different liquids, which may be done by the fluid handling infrastructure 20. The fluid handling may be controlled in an automated way by the signal processor 8 according to pre-programmed instructions and/or user input. The fluid handling infrastructure 20 includes a number of reservoirs 21 pre-filled with process liquids (RINSE/CAL1, CAL2, QC1, QC2, QC3) for rinsing/wash-out, calibration and quality control tasks. The process liquids (RINSE/CAL1, CAL2, QC1, QC2, QC3) have a known composition. The exact composition of a given batch may be stored in a chip 25 that may be attached to a cassette comprising the reservoirs 21, wherein the chip 25 may be read by the signal processor 8. The process liquid (RINSE/CAL1, CAL2, QC1, QC2, QC3) fora given process step may be selected by a fluid selector valve 22, and via feed line 12c transferred through the inlet port 6 to the sample chamber. Correct filling of the sample chamber may be monitored and verified by visual inspection or according to known procedures by observing the propagation of a liquid interface through the system by means of liquid sensors 10a, 10b, 10c located upstream and downstream of the sample chamber 2, such as at the inlet 6 ("LS inlet" 10a), at the outlet 7 ("LS BG" 10b), and just after the oxygenation measurement device 9 ("LS OXI" 10c), respectively. The fluid flow through the analyzer is driven by a pump 23, here a peristaltic hose-pump arranged downstream of the sample chamber 2 and the oxygenation measurement device 9 and connected thereto via fluid line 13. The discharged fluids are finally transported through fluid line 14 to the waste reservoir 24.

Upon start-up and, in an ongoing manner, during uptime, the analyzer 1 performs self-control routines. If any abnormality is detected, the analyzer 1 indicates the deviation to a user, and may further indicate ways of overcoming an error state. On the other hand, when the analyzer indicates normal operation, measurements can be performed immediately. Advantageously according to some embodiments, the self-control routines may be performed during idle times, i.e. when the analyzer is in an idle state, where it is not used for performing actual measurements on a user's sample. The self-control routines may include continued repetitive measurements performed on a calibration-grade process liquid with a precisely known composition, as e.g. stored on chip 25. The signals obtained for each of the different analyte sensors 3, 4 on the well-known composition may then be used to continuously update the reference for the respective analyte measurements.

A second sample space 2b with a porous membrane sensor element 110 is integrated in the downstream portion of the sample chamber 2, between the first sample space 2a and the outlet 7. The second sample space 2b is connected to the first sample space 2a through a short feed channel 102 including the flow-perturbing element 104 as an abrupt change in direction of the sample chamber 2 geometry.

FIG. 2 shows a cross-sectional detail of a sample chamber 2 for holding a complex fluid sample, the sample chamber 2 being defined by chamber walls and having an inlet 6 and an outlet 7 defining a direction of flow from the inlet 6 towards the outlet 7 for fluid handling in the sample chamber 2. The sample chamber 2 comprises a first sample space 2a and a second sample space 2b connected through a feed channel 102 comprising a flow-perturbing element 104. The flow-perturbing element 104 is thus arranged upstream of the second sample space 2b, between the first sample space 2a and the second sample space 2b.

The second sample space 2b comprises a porous membrane sensor element 110 for detecting an analyte. The porous membrane sensor element 110 has a porous membrane with a front side defining a sensor surface for contacting the fluid sample. The sensor surface faces towards the second sample space 2b, and the porous membrane comprises pores extending from respective openings at the sensor surface into the porous membrane. The pores are configured with regard to the analyte for diffusive fluid communication with the second sample space 2b. In the embodiment schematically shown here, the sensor assembly is configured for detecting multiple analytes in a whole blood sample, wherein the porous membrane sensor element 110 in the second sample space 2b is configured for detecting a high molecular weight analyte, more particularly for detecting hemoglobin as a measure for hemolysis.

The first sample space 2a comprises several further sensor elements for detecting respective further analytes, such as the ones already mentioned above. The first sample space 2a is configured for maintaining a laminar flow regime during typical fluid handling operations. The first fluid space 2a has a rectangular cross-section as seen in a cut-plane perpendicular to the principle direction from the inlet 6 to the outlet 7, wherein typical dimensions defining the channel geometry of the first sample space 2a are a width between 2 mm and 4 mm, e.g. 2.4 mm and a height between 0.3 mm and 0.5 mm, e.g. 0.4 mm.

The flow-perturbing element 104 is formed as an abrupt change in the sample chamber 2 geometry. In particular, the flow-perturbing element is formed as a connection nozzle connecting a feed channel 104 of the second sample 2b space to a downstream end of the first sample space 2a essentially perpendicular to a principal direction of the channel forming the first sample space 2a, wherein the abrupt change in the direction of the channel at the mouth of the feed channel 102 creates a flow perturbation localized in the feed channel 102. During fluid handling, when filling the sample chamber in preparation of detection measurements, the localized flow perturbation provides a mixing of the fluid sample with itself immediately prior to entering the second sample space 2b. The feed channel 102 has a length of about 2 mm as measured from the mouth of the feed channel 102 at the downstream end of the first sample space 2a to an entry orifice of the second sample space 2b. Thereby a "well-stirred" complex fluid sample is prepared immediately at the second sample space 2b.

Example

By providing a flow-perturbing element immediately upstream of a sample space for measurements using the porous membrane sensor element, an improvement in the quality of measurements for the detection of high molecular weight analytes in the continuous fraction of a complex fluid can be achieved. The improvement can be quantified by means of assessing the signal ratio between a measurement on hemolysed whole blood and on the corresponding hemolysed plasma sample (WB/P ratio). An ideal sensor construct has a WB/P ratio close to 100%.

The achieved improvement is illustrated by the following comparative data from measurements on hemolysed whole blood (HWB), which were performed for two different locations of the porous sensor element in the sample chamber. The data is summarized in two data sets given in Table 1 and Table 2, below. Each of the data sets contains measurements on three nominally identical whole blood samples with a concentration of cell free hemoglobin of 100 mg/dL (HWB100), and three corresponding hemolysed plasma samples with a concentration of cell free hemoglobin of 100 mg/dL (HWB100-Plasma), wherein the whole blood samples have a hematocrit value of 45%. The porous membrane in contact with these samples is optically probed, wherein the signal for a given sample is each time determined as the difference in absorbance at a wavelength of 416 nm and at a wavelength of 461 nm. The signal values given in the tables are expressed in arbitrary units, whereas the WP/P ratios thus determined for each of the porous membrane sensor elements, and averaged together, are expressed in percent. By moving the porous sensor element from the first location inside the first sample space to the second location in the second sample space integrated in the outlet portion of the sample chamber, an increase of the WB/P ratio from an average of 66.5% for the first location to an average of 89.4% for the second location is observed.

A first set of data, seen in Table 1, shows data from measurements with porous membrane sensors PM3, PM4, PM5, PM6, PM8, PM10, each being arranged in a first location inside the first sample space of respective sample chambers, approximately 15 mm downstream of where the inlet joins the first sample space.

TABLE 1

|  | PM3 | PM4 | PM5 | PM6 | PM8 | PM10 |
|---|---|---|---|---|---|---|
| HWB100 | 10.75 | 10.33 | 9.25 | 8.93 | 8.97 | 10.85 |
| HWB100 | 10.52 | 9.58 | 9.32 | 8.35 | 8.60 | 10.07 |
| HWB100 | 10.25 | 9.63 | 9.01 | 8.56 | 8.51 | 9.87 |
| HWB100-Plasma | 15.75 | 15.09 | 14.56 | 13.15 | 13.06 | 16.10 |
| HWB100-Plasma | 15.20 | 14.16 | 14.00 | 12.59 | 13.11 | 15.54 |
| HWB100-Plasma | 15.69 | 14.70 | 14.24 | 12.50 | 13.09 | 15.32 |
| Signal ratio between HWB100 and P100 | 67.6% | 67.2% | 64.4% | 67.6% | 66.4% | 65.6% |
| WP/P (average) | 66.5% | | | | | |

A second set of data, seen in Table 2, shows data from measurements with porous membrane sensors PM19, PM20, PM21, PM22, each arranged in a second location inside a second sample space of a respective sensor assembly, in a flow channel joining the first sample space at a right angle, and approximately 2 mm downstream of said joint. The second location of the porous membrane sensor element corresponds to the location in the second sample space as shown schematically in FIGS. 1 and 2.

TABLE 2

|  | PM 19 | PM 20 | PM 21 | PM 22 |
|---|---|---|---|---|
| HWB 100 | 9.33 | 9.41 | 10.28 | 9.14 |
| HWB 100 | 9.41 | 9.92 | 10.52 | 9.38 |
| HWB 100 | 9.74 | 10.28 | 11.01 | 9.41 |
| HWB100-Plasma | 10.45 | 11.3 | 11.42 | 10.61 |
| HWB100-Plasma | 10.59 | 11.43 | 11.41 | 10.33 |

TABLE 2-continued

|  | PM 19 | PM 20 | PM 21 | PM 22 |
|---|---|---|---|---|
| HWB100-Plasma | 10.63 | 11.32 | 11.4 | 10.83 |
| Signal ratio between HWB100 and P100 | 89.9% | 87.0% | 92.9% | 87.9% |
| WP/P (average) |  |  |  | 89.4% |

The invention claimed is:

1. A sensor assembly for analyzing a complex fluid sample, the sensor assembly comprising:
a sample chamber for holding the complex fluid sample, the sample chamber being defined by chamber walls and having an inlet and an outlet defining a direction of flow from the inlet towards the outlet in the sample chamber;
wherein the sample chamber comprises a first sample space and a second sample space,
the second sample space comprising a porous membrane sensor element for detecting an analyte; the porous membrane sensor element comprising a porous membrane with a front side defining a sensor surface for contacting the fluid sample, the sensor surface facing towards the second sample space, the porous membrane comprising dead end pores extending from respective openings at the sensor surface into the porous membrane, wherein the pores are configured with regard to the analyte for diffusive fluid communication with the second sample space,
wherein the sample chamber further comprises a flow-perturbing element arranged upstream of the second sample space, between the first sample space and the second sample space, wherein the flow-perturbing element is configured to stir the complex fluid sample at the second sample space.

2. The sensor assembly according to claim 1, wherein the porous membrane sensor element is configured for detecting a high molecular weight analyte.

3. The sensor assembly according to claim 1, wherein the first sample space comprises one or more further sensor elements for detecting respective further analytes.

4. The sensor assembly according to claim 1, wherein the flow-perturbing element is formed as a connection nozzle connecting a feed channel of the second sample space to a downstream end of the first sample space.

5. The sensor assembly according to claim 1, wherein the flow-perturbing element is formed as a connection nozzle arranged at an angle with respect to a principal axis of a sample channel forming the first sample space, wherein the angle is at least 30 degrees with respect to said principal axis.

6. The sensor assembly according to claim 1, wherein the flow-perturbing element is located upstream of the second sample space at a distance from an entry orifice of the second sample space of at least 0.3 mm and/or up to 3 mm.

7. The sensor assembly according to claim 1, wherein the sensor surface is planar.

8. The sensor assembly according to claim 1, wherein the sensor surface is arranged parallel to the direction of flow from the inlet to the outlet in the second sample space of the sample chamber.

9. The sensor assembly according to claim 1, wherein the second sample space has a cylindrical shape defined by a top wall, a bottom wall opposite to the top wall, and a circumferential wall connecting the top and bottom wall; wherein a feed orifice is arranged at an upstream end of the second sample space; wherein a discharge orifice is arranged at a downstream end thereof; and wherein the porous membrane sensor element is arranged in the top wall of the second sample space.

10. The sensor assembly according to claim 9, wherein the feed and discharge orifices are arranged in the circumferential wall opposite to each other.

11. The sensor assembly according to claim 9, wherein a height of the second sample space as seen in a direction from the top wall to the bottom wall is less than one half of a transverse dimension of the second sample space.

12. The sensor assembly according to claim 9, wherein the bottom wall is curved to reduce the distance of the bottom wall from the top wall in a center portion of the second sample space, as compared to a peripheral portion thereof.

13. The sensor assembly according to claim 1, wherein the porous membrane sensor element is configured for detecting the analyte by optical probing.

14. The sensor assembly according to claim 1, wherein the porous membrane is a translucent membrane.

15. The sensor assembly according to claim 14, wherein the porous membrane sensor element further comprises a reflective layer arranged at the front side of the translucent membrane.

16. The sensor assembly according to claim 13, wherein the porous membrane is a translucent membrane, wherein the porous membrane sensor element further comprises
an optical input port connected to a back side of the translucent membrane, the back side facing away from the front side, optical input port being adapted for feeding probing light to a probing region of the translucent membrane through the back side; and
an optical output port connected to the back side of the translucent membrane, the optical output port being adapted for collecting an optical response from the translucent membrane through the back side.

17. The sensor assembly according to claim 1, wherein the flow-perturbing element is located upstream of the second sample space at a distance from an entry orifice of the second sample space of at least 1 mm.

18. The sensor assembly according to claim 1, wherein the flow-perturbing element is located upstream of the second sample space at a distance from an entry orifice of the second sample space of up to 10 mm.

19. A sensor assembly for analyzing a complex fluid sample, the sensor assembly comprising:
a sample chamber for holding the complex fluid sample, the sample chamber being defined by chamber walls and having an inlet and an outlet defining a flow path from the inlet to the outlet in the sample chamber;
wherein the sample chamber comprises a first sample space and a second sample space,
the second sample space comprising a porous membrane sensor element for detecting an analyte, the porous membrane sensor element being positioned within the flow path,
wherein the sample chamber further comprises a flow-perturbing element arranged upstream of the second sample space.

* * * * *